United States Patent
Enders et al.

(10) Patent No.: US 11,801,112 B2
(45) Date of Patent: Oct. 31, 2023

(54) METHOD FOR MONITORING CONSUMABLES DURING A MEDICAL PROCEDURE AND MEDICAL IMAGE PROCESSING SYSTEM

(71) Applicant: Olympus Winter & Ibe GmbH, Hamburg (DE)

(72) Inventors: Borg Enders, Hamburg (DE); Thorsten Juergens, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 238 days.

(21) Appl. No.: 17/478,104

(22) Filed: Sep. 17, 2021

(65) Prior Publication Data
US 2022/0087770 A1 Mar. 24, 2022

(30) Foreign Application Priority Data
Sep. 21, 2020 (DE) ...................... 10 2020 124 551.3

(51) Int. Cl.
*A61B 90/00* (2016.01)
(52) U.S. Cl.
CPC ...... *A61B 90/08* (2016.02); *A61B 2090/0803* (2016.02); *A61B 2090/0805* (2016.02)
(58) Field of Classification Search
CPC .......................... A61B 90/08; A61B 2090/0803
USPC ............................................................ 606/1
See application file for complete search history.

(56) References Cited

U.S. PATENT DOCUMENTS

| | | | |
|---|---|---|---|
| 2004/0186683 A1* | 9/2004 | Farber | G06Q 10/087 606/1 |
| 2009/0317002 A1 | 12/2009 | Dein | |
| 2010/0081921 A1 | 4/2010 | Urban et al. | |

FOREIGN PATENT DOCUMENTS

| | | |
|---|---|---|
| DE | 10 2011 050 006 A1 | 10/2012 |
| EP | 2 169 576 A1 | 3/2010 |
| WO | 2013/070823 A1 | 5/2013 |

OTHER PUBLICATIONS

German Office Action dated Jul. 16, 2021 received in 10 2020 124 551.3.
"Every Swab Counts," https://www.aps-ev.de/wp-content/uploads/2016/09/Glossar_JTZ_Internet.pdf.
Japanese Office Action dated Sep. 6, 2022 received in 2021-144219.

* cited by examiner

*Primary Examiner* — Nadia A Mahmood
(74) *Attorney, Agent, or Firm* — Scully, Scott, Murphy & Presser, P.C.

(57) ABSTRACT

A method for monitoring consumables during a medical procedure, wherein unused consumables are provided in a supply area, consumables are used in a surgery area, and used consumables are deposited in a collection area. The method including: observing the supply area and the collection area with at least one first camera, registering, by a first automatic image processing method, when unused consumables are removed from the supply area, registering, by a second automatic image processing method, when used consumables are deposited in the collection area, and balancing the consumables removed from the supply area and the consumables deposited in the collection area.

10 Claims, 4 Drawing Sheets

METHOD FOR MONITORING CONSUMABLES DURING A MEDICAL PROCEDURE AND MEDICAL IMAGE PROCESSING SYSTEM

CROSS-REFERENCE TO RELATED APPLICATION

The present application is based upon and claims the benefit of priority from DE 10 2020 124 551.3 filed on Sep. 21, 2020, the entire contents of which is incorporated herein by reference.

BACKGROUND

Field

The present disclosure relates to a method for monitoring consumables during a medical procedure and a medical image processing system.

Prior Art

Consumables are used in many medical procedures, especially surgical procedures. Consumables can be auxiliary materials that are provided for one-time use during the respective procedure and are disposed of after use.

A typical example of consumables are surgical swabs, which are used during surgical procedures to collect blood and other body fluids in the surgical site to ensure good visibility for the surgeon.

Depending on the amount of fluid during the procedure, such a swab can remain in the surgical site for a longer period of time, e.g., to collect small seepage amounts of blood, or it may be removed again after a short period of time, e.g., in case of heavy bleeding.

In any case, it must be ensured at the end of a procedure that no consumables are accidentally left in the surgical site when it is closed. Consumables left in the surgical site can cause persistent discomfort, delayed wound healing, or even more serious complications such as infection.

According to studies, despite strict regulations for completeness control in body cavity surgical procedures, there are approximately 20 incidents per 100000 procedures in which consumables are unintentionally left in the surgical site ("Every Swab Counts," https://www.aps-ev.de/wp-content/uploads/2016/09/Glossar_JTZ_Internet.pdf).

SUMMARY

It is an object to provide methods and systems that significantly reduce the risk of consumables being forgotten in the surgical site.

Such object can be achieved by a method for monitoring consumables during a medical procedure, wherein unused consumables are provided in a supply area, consumables are used in a surgery area, and used consumables are deposited in a collection area, the method comprising: observing the supply area and the collection area with at least one camera, registering, by means of a first automatic image processing method, when unused consumables are removed from the supply area, registering, by means of a second automatic image processing method, when used consumables are deposited in the collection area, and balancing the consumables removed from the supply area and the consumables deposited in the collection area.

The use of automatic image processing methods eliminates human sources of error in the balancing of consumables. In this context, end-to-end monitoring can be particularly reliable, since the respective supply and collection areas can generally be easily captured by cameras. Detection errors due to overlapping of the relevant areas, e.g., by persons in the field of view of the cameras, can thus be prevented.

As automatic image processing methods, classical image processing methods may be used, which recognize targeted objects on the basis of predefined rules. Alternatively, image processing methods based on artificial intelligence may be used.

In addition, the surgery area may be monitored with at least one camera and by means of a third automatic image processing method it may be determined at which location in the surgery area registered consumables are introduced, and/or from which location in the surgery area registered consumables are removed. This makes it possible, when a deficit of consumables is detected, to automatically determine at which point in the surgery area consumables may still be presumed to be present. Locating missing consumables may thus be accelerated.

In an embodiment of a method, the consumables may be countable consumables, and a consumable counter may be maintained, which is set to 0 at the beginning of the medical procedure; increased when registering the removal of a consumable from the supply area; and decreased when registering the deposition of a consumable in the collection area. The consumables counter thus indicates at any time how many consumables are present in the surgery area.

At the same time, after completion of the medical procedure, the value of the counter may be output. For example, after completion of the procedure, a consumable log may be generated as a verification document that explicitly states the value of the consumable counter.

In another embodiment of a method, a still image may be recorded and stored when the introduction and/or removal of a consumable into or from the surgery area is registered. Storing such still images enables manual rechecking of the consumable count in case of discrepancies.

Likewise, a video sequence of predetermined or predeterminable length may be recorded and stored when the introduction and/or removal of a consumable into or from the surgery area is registered. Video sequences may provide further information in the event of a manual recheck of the consumable count, or enable more accurate identification.

The consumable material can be introduced and/or removed by means of one or more surgical gripping instruments, and it may be detected by means of the third automatic image processing method whether a surgical gripping instrument with or without consumables is introduced into the surgery area and/or removed from the surgery area. Taking surgical gripping instruments into account may provide additional information to the automatic image processing methods to increase the detection rate for consumables.

The first and/or second automatic image processing methods may be configured to recognize when more than one piece of countable consumables are simultaneously removed from the supply area or deposited in the collection area.

In this context, the first automatic image processing method may be configured to determine the number of consumables removed on the basis of characteristic geometric data. This may be, for example, the change in height of a supply stack, or the contour of fold lines if the consumables are held in folded form.

The countable consumables may be manually separated in the collection area, and the second automatic image processing method may be configured to determine the number of deposited consumables after the separation. The separation, which is often mandatory in the collection area anyway, greatly simplifies the determination of the number of consumables deposited in each instance.

Such object can also be achieved by a medical image processing system comprising: one or more cameras configured to detect a supply area for unused consumables, a collection area for used consumables, and optionally a surgery area; and a controller configured to receive video data from the one or more cameras; wherein the controller is configured to perform a method according to the preceding embodiments. With respect to the effects and advantages achievable thereby, explicit reference is made to the aforesaid.

BRIEF DESCRIPTION OF THE DRAWINGS

In the following, the embodiments will be explained in more detail by means of some exemplary embodiments. In this regard, the illustrated embodiments are merely intended to contribute to a better understanding of the invention without limiting it, in which.

DETAILED DESCRIPTION

Figure 1:
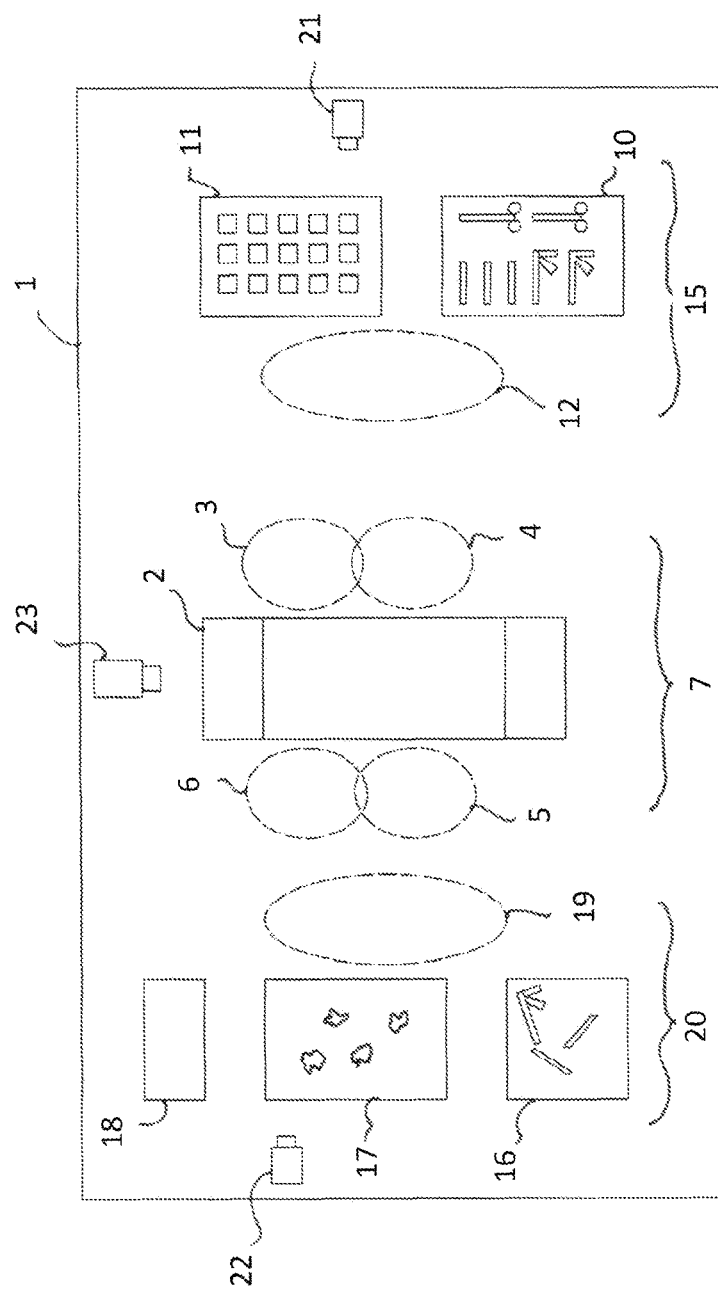
FIG. 1 illustrates a structure of an operating room in a simplified representation.

FIG. 1 shows an exemplary layout of an operating room 1 in a highly simplified top view. An operating table 2 is located approximately in the center of the operating room 1, on which an operation can be performed. Around the operating table 2, movement areas 3, 4, 5, 6 of persons directly involved in an operation to be performed are indicated. The operating table 2 and the movement areas 3, 4, 5, 6 form a surgery area 7.

In FIG. 1, supply tables 10, 11 are shown to the right of the surgery area 7. Various surgical instruments are disposed on the supply table 10, and several supply stacks with medical consumables are located on the supply table 11, in the example shown, swabs for collecting blood and other fluids. Between the supply tables 10, 11 and the surgery area 7, the movement area 12 of an assistant is indicated, who takes surgical instruments and/or consumables from the supply tables 10, 11 and hands them to the persons directly involved in the operation. The supply tables 10, 11 and the movement area 12 form a supply area 15.

In FIG. 1 to the left of the surgery area 7 are deposit tables 16, 17 and a discharge container 18. Used surgical instruments may be deposited on the deposit table 16. Used consumables may be deposited on the deposit table 17 and separated for balancing purposes. After separation and balancing, the consumables may be placed in the discharge container 18. As a general rule, the consumables are not placed in the discharge container 18 until the operation has been completed in order to allow recounting in the event of inconsistencies during balancing. A movement area 19 of a further assistant is indicated between the deposit tables 16, 17 and the discharge container 18 on the one hand and the surgery area 7 on the other hand, who receives used surgical instruments as well as consumables. The deposit tables 16, 17, the discharge container 18, and the movement area 19 form a collection area 20.

The positions of supply area 15 and collection area 20 relative to surgery area 7 may vary depending on the type of procedure, and the configuration shown is merely one possible example to illustrate each function. In many cases, the supply tables 10, 11 will be configured as a single table. It is also not unusual to combine the supply area 15 and the collection area 20 so that supply and collection of the material can be performed by a single assistant.

In order to ensure that no surgical instruments and consumables are unintentionally left in the patient after a procedure, such as after an open procedure in a body cavity of a patient, the surgical instruments and consumables are balanced, i.e., it is monitored that all instruments and consumables removed from the supply area 15 are also dispensed in the collection area 20. This balancing is usually done manually, and is therefore prone to error. For example, in the case of emergency operations, unplanned changes to the surgical procedure or a change of personnel during the operation, balancing errors can occur, as a result of which objects such as surgical instruments or consumables unintentionally remain in the patient. While the risk of this happening with surgical instruments is rather low as they are easily recognizable visually, there is an increased risk for consumables such as swabs, as they are hardly easily recognizable within a body cavity, especially after contact with blood.

In order to make the balancing of the consumables independent from human influences, cameras 21, 22 are disposed in the supply area 15 and in the collection area 20 to monitor the respective areas or to send video images of the corresponding areas to a control system not shown in FIG. 1.

In the control system, several automatic image processing procedures are executed in parallel to each other, which evaluate the video images supplied by the cameras 21,22 in order to register the removal of consumables from the supply area 15 and/or the deposit of consumables in the collection area.

Another camera 23 may be provided in the surgery area to send video images from the surgery area to the controller as well. There, an additional automatic image processing procedure may evaluate at which location in the surgery area consumables are placed and/or removed.

Figure 2:
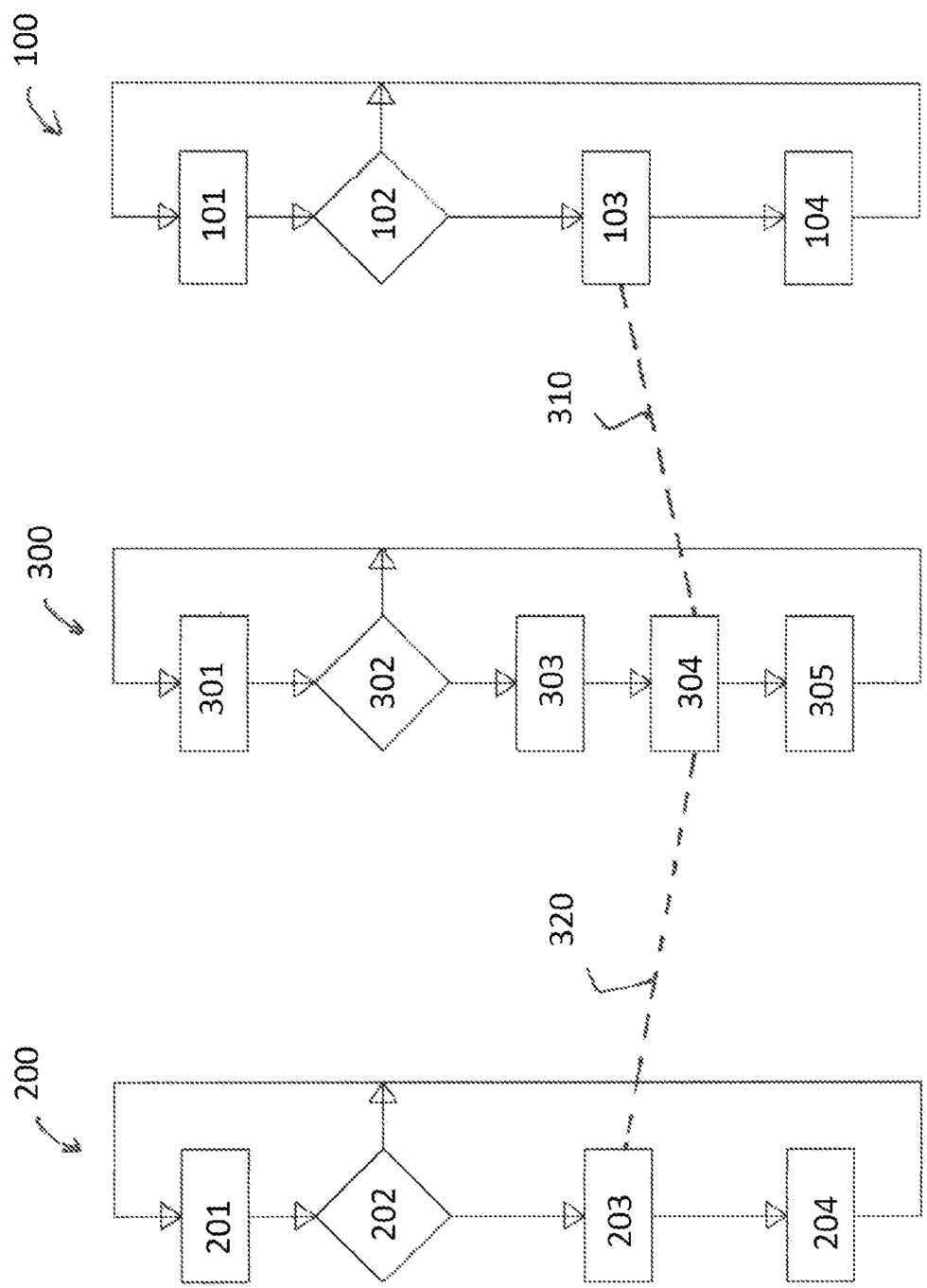
FIG. 2 illustrates a balancing method.

In addition, the control system executes a consumables balancing procedure, which is divided into three independent subprocesses shown in FIG. 2. The balancing procedure uses a single consumables counter, which is defined in the controller, e.g., as a variable, and is set to 0 at the beginning of a procedure.

A first subprocess 100 processes information from the supply area 15. In a first step 101, a video image or a short video sequence is received from the camera 21. In a further step 102, it is queried whether the video image or video sequence shows consumables being removed from the supply area 15. If this is not the case, the sub-process 100 starts again at step 101 to receive another image or video sequence.

If, on the other hand, it is determined at step 102 that consumables have been removed, then at step 103 it is determined how many pieces of countable consumables have been removed. In step 104, the consumables counter is then incremented by the corresponding number. This indicates that the number of consumables in question has been removed from the supply area, and thus may potentially be present within the patient's body. Subsequently, subprocess 100 starts again at step 101.

A second subprocess 200 processes information from the collection area 20. In a first step 201, a video image or a short video sequence is received from the camera 22. In a further step 202, it is queried whether the video image or video sequence shows consumables being deposited in the collection area 20. If this is not the case, the sub-process 200 starts again at step 201 to receive another image or video sequence.

If, on the other hand, it is determined at step 202 that consumables have been deposited, then at step 203 it is determined how many pieces of countable consumables have been deposited. In step 204, the consumable counter is then decreased by the corresponding number. This indicates that the number of consumables in question has been removed from the surgery area and thus can no longer potentially be present within the patient's body. Subsequently, subprocess 200 begins again at step 201.

A third sub-process 300 processes information from the surgery area 7, where again in a first step 301 a video image or a short video sequence is received from the camera 23. In a further step 302, it is queried whether the video image or video sequence shows the introduction or removal of consumables into or from the surgery area 7. If not, subprocess 300 also starts again at step 301 to receive another image or video sequence.

Unlike sub-processes 100, 200, sub-process 300 determines at step 303 at which position in the surgery area the consumable was inserted or removed. For this purpose, a virtual position grid is defined that covers the surgery area, and a separate consumable counter is provided for each field of the grid.

In step 304, it is then determined again how many pieces of the consumable were introduced or removed. In step 305, the consumable counter associated with the position determined in step 303 is incremented or decremented by the number determined in step 304 to indicate how many pieces of consumable are currently in each location of the surgery area.

After completion of the procedure, which may be indicated to the controller, for example manually via an input device, the value of the consumable counter may be output via a suitable output device, this may be a monitor or other display. If the value of the consumable counter is not 0 when the operation is completed, an error signal and/or an alarm may also be output.

If the sub-processes 100, 200, 300 work with video sequences instead of single images, the length of these sequences may be selected in such a way that, on the one hand, the data volume to be processed remains manageable and, on the other hand, a meaningful statement about trajectories remains possible. Reasonable sequence lengths can be between 1 second and 5 seconds, for example. If sequences are too long, there is a risk that several relevant events are present in a sequence and that not all of them may be recognized.

The image processing procedures required for the individual sub-processes 100, 200, 300 vary in complexity due to the different requirements. In principle, known image processing operations are used, which the skilled person selects from his professional expertise according to the respective requirements. Besides deterministic algorithms, non-deterministic methods which are commonly summarized under the term "artificial intelligence" (AI) may also be used for sub-tasks or for all of the image processing procedures. In this context, neural networks, such as convolutional neural networks, are particularly suitable for the image processing tasks of object recognition and object classification. Such networks can be trained with training data in the form of video images or video sequences showing the removal or deposition of unused or used consumables, which have been pre-evaluated by manual classification.

The examination to be performed in steps 102 and 202, respectively, to determine whether consumables are removed or deposited is relatively straight-forward. Both unused and used swabs or similar consumables may easily be identified visually against the background of, for example, a stainless steel table, and known object recognition algorithms may be used for this purpose. When evaluating video sequences, trajectories of identified objects may additionally be determined; a removal or deposition may then be considered reliably identified if, for example, the trajectory of an identified object crosses a predetermined demarcation line, e.g., the edge of the respective table.

Figure 3A:
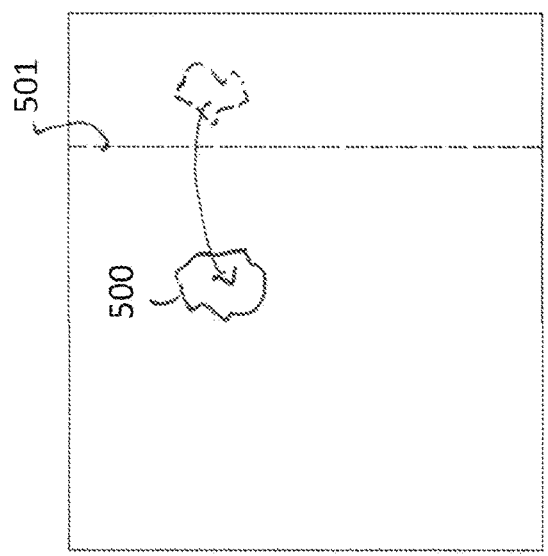
FIGS. 3a and 3b illustrate optical scenarios in a supply area.
Figure 3B:
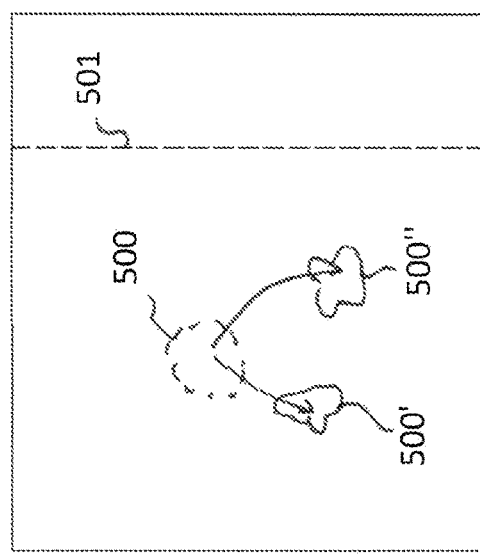

FIGS. 3a, 3b show two possible scenarios which may occur in the supply area 15. FIG. 3a shows how a stack 400 of consumables is moved on the supply table 11, for example to allow easier access. In doing so, the stack 400 does not cross the demarcation line 401, consequently no removal of material is detected.

In FIG. 3b, however, a part 402 is removed from the stack 400 and moved across the demarcation line 401. The controller therefore registers the removal of consumables. The number of pieces of consumable material actually removed may be determined relatively easily, for example, by determining the height of the stack 400 before and after removal from an image recorded at an angle. Alternatively, geometric features of the consumable may be evaluated, such as characteristic fold spines of folded materials, or similar features.

Figure 4A:
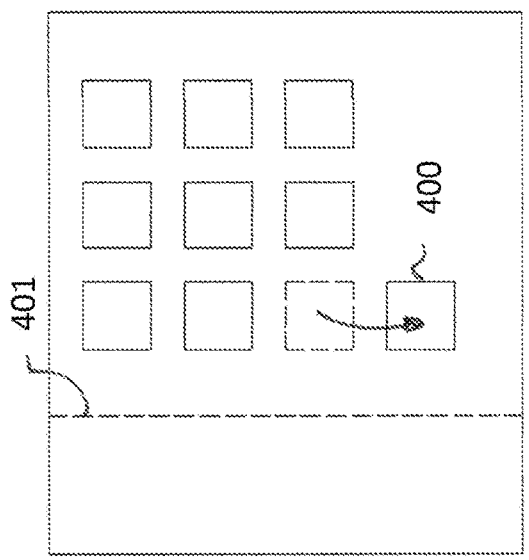
FIGS. 4a and 4b illustrate optical scenarios in a collection area.
Figure 4B:
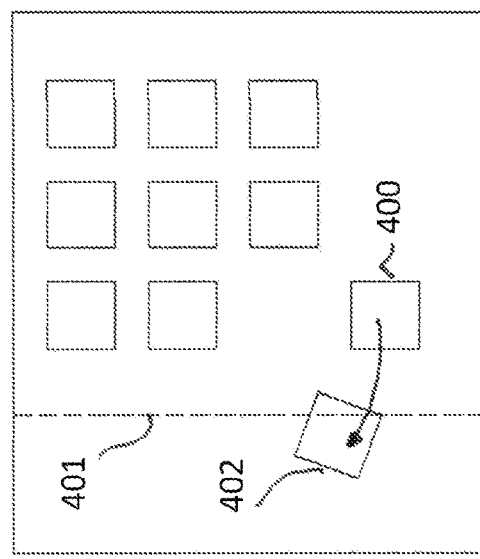

FIGS. 4a, 4b illustrate two possible scenarios in the collection area 20. FIG. 4a shows how a lump 500 of consumables is placed on the deposit table 17 via a demarcation line 501. The controller classifies this as a deposit of consumables. FIG. 4b shows how the lump 500 of consumables is subsequently separated into two pieces 500', 500". Here, no consumable is moved across the demarcation line 501, so no new deposit is registered. However, the control system may recognize from the separation that two pieces of consumable material were actually deposited previously, and account for this accordingly.

In the sub-process 200, other methods may be used to accurately determine the number of pieces of consumable material deposited. For example, the camera 22 may be a stereo camera or a TOF camera for this purpose, so that the volume of the lump 500 of consumables may additionally be estimated from the video data. Since the volume of a single piece of consumable is known, the actual volume may also be used to infer the number of pieces of consumable present in the lump 500.

The video data to be processed to the subprocess 300 is fundamentally more difficult to evaluate than the data to be processed in the subprocesses 100, 200. On the one hand, this is due to the fact that in the surgery area it is hardly possible to arrange the camera 23 in such a way that its field of view is not occasionally obscured by the persons involved in the procedure. On the other hand, the image background, which depicts an opened body cavity, for example, does not provide a sharp contrast with regard to the pieces of used consumables. In order to nevertheless extract reasonably reliable information about the distribution of consumables, additional image elements may be evaluated. For example, consumables are usually inserted and removed using gripping instruments, which can be found relatively easily using image processing methods. Once a gripping instrument has been detected, further image analysis may also be used to easily determine whether the respective instrument is currently loaded with consumables. By evaluating this information, the location of the consumables may be indirectly determined.

In order to determine the respective number of pieces of consumable introduced or removed, the sub-process 300 may rely on information from the sub-processes 100, 200, this is indicated in FIG. 2 by the dashed lines 310, 320.

The primary function of balancing the consumables is realized in the subprocesses 100, 200. In these sub-processes, high detection reliability is ensured because of the good optical conditions, so that the accuracy of automatic balancing easily exceeds that of manual balancing.

Regarding the subprocess 300, there is a higher probability of detection errors because of the poorer optical conditions. Therefore, the results of this sub-process are not used directly for balancing, but are only used to find missing consumables more quickly in the event of deviations during balancing.

For tracking purposes, video data from cameras 21, 22, 23 can be stored in full or in part. If, after completion of an operation, doubts arise as to the correct balancing, this may thus be checked manually or automatically using the stored video data. In order to reduce the volume of data to be stored, for example, only those video images or video sequences may be stored on which a removal, deposition, or separation is recognizable.

Figure 5:
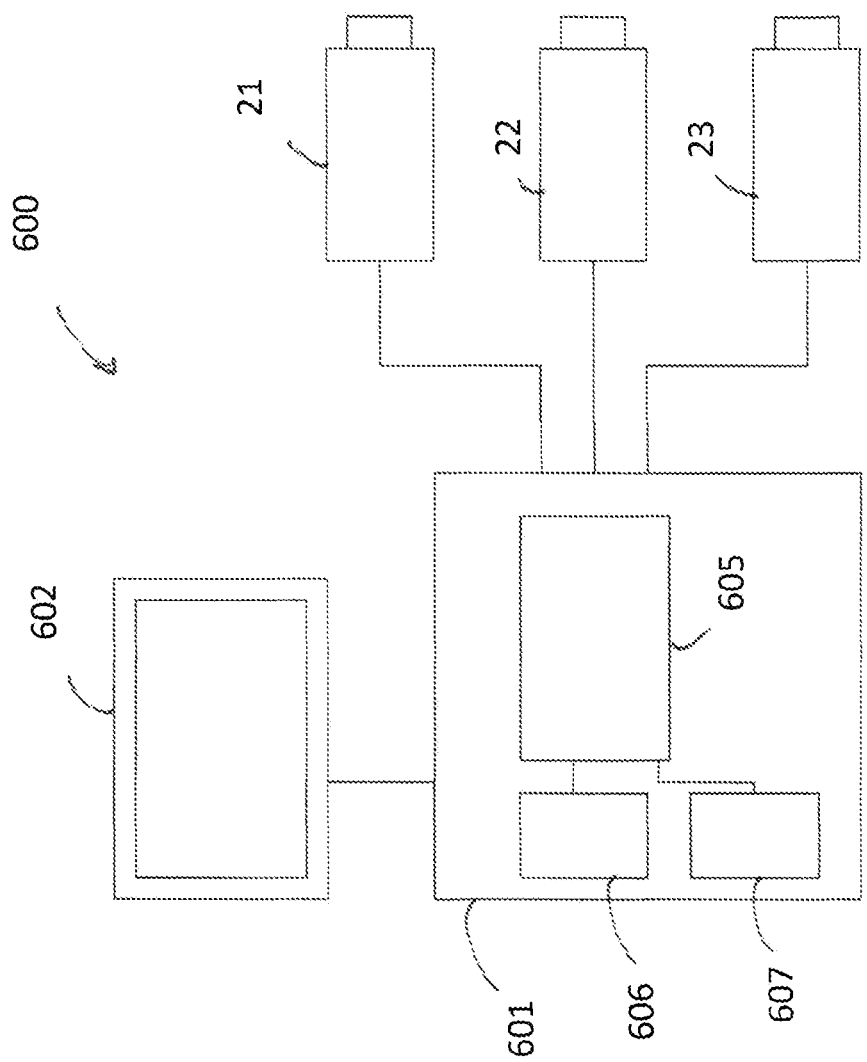
FIG. 5 illustrates an image processing system.

FIG. 5 illustrates a medical image processing system 600. The image processing system 600 comprises cameras 21, 22, 23, a controller 601, and a monitor 602.

The controller 601 includes a processor 605, a program memory 606, and a working memory 607.

The program memory 606 contains program information that is read and executed by the processor 605 to perform the procedures described above. In this regard, the processor 605 may be a standard processor. To achieve the highest possible processing speed, the processor 605 may be a multi-core processor capable of executing the sub-processes 100, 200, 300 in parallel, in whole or in part. Multiprocessor systems with multiple CPUs may also be used. When AI-based processes are applied, graphics processing units (GPUs) optimized specifically for such processes may be used. The video data from the cameras 21, 22, 23 is stored in the main memory 607 during processing.

The monitor 602 is used to output the balance result after the operation is completed.

The above description represents only one possible embodiment, and may be modified within the scope of the appended claims. For example, if the surgery area 7, supply area 15 and collection area 20 are suitably arranged, less than three cameras may be required, and in the most favorable case, one camera may be sufficient. The camera provided for the surgery area may be a room camera present in modern operating rooms.

Even though the embodiments are described here only in connection with open surgical procedures, it may equally be used for minimally invasive procedures performed with endoscopic instruments.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A method for monitoring consumables during a medical procedure, wherein unused consumables are provided in a supply area, consumables are used in a surgery area, and used consumables are deposited in a collection area, the method comprising:
    observing the supply area and the collection area with at least one first camera,
    registering, by a first automatic image processing method, when unused consumables are removed from the supply area,
    registering, by a second automatic image processing method, when used consumables are deposited in the collection area, and
    balancing the consumables removed from the supply area and the consumables deposited in the collection area;
    wherein one or more of the first and second automatic image processing method is configured to recognize when more than one piece of countable consumables are simultaneously removed from the supply area or deposited in the collection area; and
    the first automatic image processing method is configured to determine the number of consumables removed on the basis of characteristic geometric data.

2. The method according to claim 1, further comprising:
    monitoring the surgery area with at least one second camera, and
    determining by a third automatic image processing method one or more of at which location in the surgery area registered consumables are introduced and from which location in the surgery area registered consumables are removed.

3. The method according to claim 1, wherein the consumables are countable consumables, wherein the balancing comprises maintaining a consumables counter which
    is set to 0 at the beginning of the medical procedure,
    is incremented when registering the removal of a consumable from the supply area, and
    is decreased when registering the deposition of a consumable in the collection area.

4. The method according to claim 3, further comprising outputting a value of the counter after completion of the medical procedure.

5. The method according to claim 2, further comprising recording and storing a still image when one or more of the introduction and removal of a consumable into or from the surgery area is registered.

6. The Method according to claim 2, further comprising recording and storing a video sequence of predetermined length when one or more of the introduction and removal of a consumable into or from the surgery area is registered.

7. The method according to claim 2, further comprising:
    one or more of introducing and removing the consumables using one or more surgical gripping instruments and
    detecting, with the third automatic image processing method, whether a surgical gripping instrument from the one or more surgical gripping instruments is one or more of introduced and removed from the surgery area with or without consumables.

8. The method according to claim 1, wherein countable consumables are manually separated in the collection area, and the second automatic image processing method is configured to determine the number of deposited consumables after the separation.

9. A medical image processing system, comprising:
one or more first cameras configured to capture a supply area for unused consumables and a collection area for used consumables, and
a controller configured to,
  receiving first video data from the one or more first cameras,
  observing the supply area having unused consumables and the collection area having used consumables with the one or more first cameras,
  registering, by a first automatic image processing method, when the unused consumables are removed from the supply area,
  registering, by a second automatic image processing method, when the used consumables are deposited in the collection area, and
  balancing the consumables removed from the supply area and the consumables deposited in the collection area;
wherein one or more of the first and second automatic image processing method is configured to recognize when more than one piece of countable consumables are simultaneously removed from the supply area or deposited in the collection area; and
the first automatic image processing method is configured to determine the number of consumables removed on the basis of characteristic geometric data.

10. The medical image processing system according to claim 9, further comprising at least one second camera configured to monitor a surgical area,
wherein the controller is further configured to:
receive second video data from the at least one second camera, and
determine by a third automatic image processing method one or more of at which location in the surgery area registered consumables are introduced and from which location in the surgery area registered consumables are removed.

* * * * *